United States Patent
Cinader, Jr. et al.

(10) Patent No.: US 8,738,165 B2
(45) Date of Patent: May 27, 2014

(54) METHODS OF PREPARING A VIRTUAL DENTITION MODEL AND FABRICATING A DENTAL RETAINER THEREFROM

(75) Inventors: David K. Cinader, Jr., Walnut, CA (US); David W. Kuhns, Monrovia, CA (US); Oliver L. Puttler, La Crescenta, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 521 days.

(21) Appl. No.: 12/808,214

(22) PCT Filed: Dec. 17, 2008

(86) PCT No.: PCT/US2008/087060
§ 371 (c)(1),
(2), (4) Date: Aug. 27, 2010

(87) PCT Pub. No.: WO2009/085781
PCT Pub. Date: Jul. 9, 2009

(65) Prior Publication Data
US 2011/0004331 A1    Jan. 6, 2011

Related U.S. Application Data

(60) Provisional application No. 61/015,945, filed on Dec. 21, 2007.

(51) Int. Cl.
*G05B 11/01* (2006.01)
*A61C 3/00* (2006.01)
*G06F 19/00* (2011.01)

(52) U.S. Cl.
USPC ............................... 700/98; 433/24; 700/182

(58) Field of Classification Search
CPC ...... A61C 13/0004; A61C 7/00; G06F 3/016; G06F 17/50

USPC ............. 700/98, 182; 433/24, 213–215, 233; 382/278

See application file for complete search history.

(56) References Cited

U.S. PATENT DOCUMENTS

| 2,531,222 A | 11/1950 | Kesling |
| 3,271,858 A | 9/1966 | Simmons |

(Continued)

FOREIGN PATENT DOCUMENTS

| EP | 0 097 001 | 12/1983 |
| EP | 1 570 803 | 9/2005 |

(Continued)

OTHER PUBLICATIONS

U.S. Appl. No. 61/015934, filed entitled "Orthodontic Treatment Monitoring Based on Reduced Images", filed Dec. 21, 2007.

(Continued)

*Primary Examiner* — Mohammad Ali
*Assistant Examiner* — Ziaul Karim
(74) *Attorney, Agent, or Firm* — Kevin W. Weber (57) ABSTRACT

A virtual model of a dental patient's dentition is provided by obtaining a digital data file of the patient's teeth and orthodontic appliances connected to the teeth, and then combining data from the data file with other data that represents surfaces of the teeth underlying the appliances. The virtual model is useful in preparing a physical model of the patient's current dentition that can be used, for example, to make a dental retainer. Advantageously, the retainer can be fabricated before the orthodontic appliances are disconnected from the patient's teeth and ready for use as soon as the patient's teeth have reached their desired positions in the oral cavity.

21 Claims, 4 Drawing Sheets

(56) References Cited

U.S. PATENT DOCUMENTS

| | | |
|---|---|---|
| 3,994,068 A | 11/1976 | Goshgarian |
| 4,672,032 A | 6/1987 | Slavkin |
| 4,798,534 A | 1/1989 | Breads |
| 4,976,614 A | 12/1990 | Tepper |
| 5,204,055 A | 4/1993 | Sachs |
| 5,340,656 A | 8/1994 | Sachs |
| 5,387,380 A | 2/1995 | Cima |
| 5,490,882 A | 2/1996 | Sachs |
| 5,490,962 A | 2/1996 | Cima |
| 5,518,680 A | 5/1996 | Cima |
| 5,700,289 A | 12/1997 | Breitbart |
| 6,210,162 B1 | 4/2001 | Chishti |
| 6,217,334 B1 | 4/2001 | Hultgren |
| 6,227,851 B1 | 5/2001 | Chishti |
| 6,394,801 B2 | 5/2002 | Chishti |
| 6,398,548 B1 | 6/2002 | Muhammad |
| 6,497,574 B1 | 12/2002 | Miller |
| 6,540,512 B1 | 4/2003 | Sachdeva |
| 6,554,611 B2 | 4/2003 | Chishti |
| 6,612,143 B1 | 9/2003 | Butscher |
| 6,632,089 B2 * | 10/2003 | Rubbert et al. ............ 433/24 |
| 6,648,640 B2 | 11/2003 | Rubbert |
| 6,821,462 B2 | 11/2004 | Schulman |
| 6,928,733 B2 | 8/2005 | Rubbert |
| 7,076,980 B2 | 7/2006 | Butscher |
| 7,134,874 B2 | 11/2006 | Chishti |
| 7,241,142 B2 | 7/2007 | Abolfathi |
| 7,435,084 B2 | 10/2008 | Liu |
| 8,359,114 B2 * | 1/2013 | Steingart et al. ............ 700/98 |
| 2002/0010568 A1 * | 1/2002 | Rubbert et al. ............ 703/6 |
| 2003/0021453 A1 | 1/2003 | Weise |
| 2003/0207227 A1 | 11/2003 | Abolfathi |
| 2004/0073417 A1 * | 4/2004 | Rubbert et al. ............ 703/11 |
| 2005/0040551 A1 | 2/2005 | Biegler |
| 2006/0263738 A1 | 11/2006 | Kuo |

FOREIGN PATENT DOCUMENTS

| | | |
|---|---|---|
| WO | 01/84479 | 11/2001 |
| WO | WO 2005/115266 | 12/2005 |
| WO | WO 2009/042378 | 4/2009 |

OTHER PUBLICATIONS

Search Report for PCT/US2008/087060, mailed Aug. 21, 2009.

Jost-Brinkmann et al., "Computer-Aided Fabrication of Bonded Lingual Retainers", J. Clinical Orthodontics, vol. XXX, No. 10, 1996, pp. 559-563.

Sassani et al., "Computer-Assisted Fabrication of Orthodontic Appliances: Considering the Possibilities", J. of American Dental Assoc., vol. 126, Sep. 1995, pp. 1296-1300.

Willison, Practical Guide to Orthodontic Appliances: a comprehensive resource from theory to fabrication, Tonawanda, New York, Great Lakes Orthodontics, pp. 593-599, 2004.

Search Report CN Application No. 200880127342.2 Aug. 30, 2012, 1 page.

* cited by examiner

METHODS OF PREPARING A VIRTUAL DENTITION MODEL AND FABRICATING A DENTAL RETAINER THEREFROM

CROSS REFERENCE TO RELATED APPLICATIONS

This application is a national stage filing under 35 U.S.C. 371 of PCT/US2008/087060, filed Dec. 17, 2008, which claims priority to U.S. Provisional Application Ser. No. 61/015,945, filed Dec. 21, 2007, the disclosure of which is incorporated by reference in its entirety herein.

BACKGROUND OF THE INVENTION

1. Field of the Invention

This invention broadly relates to the use of digital data in the practice of dental methods. More particularly, the present invention relates to methods of preparing virtual dentition models and methods of fabricating dental appliances such as retainers from virtual models.

2. Description of the Related Art

A wide variety of dental appliances are known in the art. Some types of dental appliances are used in orthodontic treatment to move crowded, crooked or misaligned teeth to correct positions in the oral cavity. Other types of dental appliances include retainers, which are often used to maintain the position of the patient's teeth following orthodontic treatment.

Orthodontic treatment is often carried out by the use of tiny slotted appliances known as brackets that are secured to the patient's teeth by an adhesive. A resilient archwire is placed in the slot of each bracket and forms a track to guide movement of the teeth to desired locations. Ends of the archwire are often connected to small appliances known as buccal tubes that are secured to the patient's molar teeth. In some instances, brackets and buccal tubes are not directly bonded to the surfaces of the patient's teeth but are instead welded or brazed to small metallic bands that, in turn, are placed over the corresponding teeth in encircling relation.

Often, a set of brackets, buccal tubes and archwire is provided for each of the patient's upper and lower dental arches. The brackets, buccal tubes and archwires are commonly referred to collectively as "braces". In many instances, braces are worn by patients for a period of time extending from one to two years.

Once the patient's teeth have reached their final desired positions as a result of the corrective forces provided by the braces, the braces (including the brackets, archwires, buccal tubes and other components) are removed from the patient's teeth. However, at this point in time the patient's teeth are often relatively mobile and may tend to move toward previous positions in the dental arches if not held in place. For this reason, dental retainers are often used at the conclusion of orthodontic treatment to immobilize the teeth until such time as sufficient bone structure has grown along roots of the teeth to retain the teeth in desired positions.

Dental retainers are commonly fabricated by commercial dental laboratories using a plaster of Paris or "stone" model of the patient's teeth that resembles the appearance of the teeth in their final or finish positions. Often, retainers are made using thermoplastics such as acrylics, ethylene/propylene copolymers, polyvinylchloride, polycarbonate and polyethylene terepthalate. Thermosetting acrylics are also used. Dental retainers often also incorporate metallic members such as wires, springs and frameworks for engagement with the teeth. Some types of dental retainers are removable by the patient when desired such as during mealtimes, while other types of dental retainers are fixed in place by, for example, an adhesive.

Certain types of dental retainers are fabricated by placing a custom-bent wire on the stone model. Next, a quantity of an acrylic material is arranged along portions of the wire to form the body of the retainer for placement next to the patient's palate. After the acrylic has hardened, the retainer is removed from the stone model and trimmed as desired. The retainer is then polished and shipped to the orthodontic practitioner.

It is often deemed best for an orthodontic patient to wear a retainer as soon as the braces have been removed from the patient's mouth. For this reason, it is desirable to begin fabrication of the customized retainer while the patient is still wearing braces so that the retainer is available at the practitioner's office immediately after the braces have been removed from the patient's mouth. To this end, an impression of the patient's teeth while wearing braces is often taken approximately one or two months before the estimated completion of orthodontic treatment so that a stone model of the patient's dentition can be prepared and used to fabricate the custom retainer.

However, the practice of taking an impression of the patient's teeth while wearing braces often presents difficulties. For example, the impression material often extends into recesses, cavities and other structure of the brackets, buccal tubes and archwires and hardens. As the impression material is removed from the patient's oral structure, the impression material may tear or fracture in areas adjacent the orthodontic appliances, which may cause areas of distortion of the resulting stone model. In some instances, removal of the impression material may also bend or distort the orthodontic components or cause the components to detach from the teeth.

In addition, when an impression is taken while the patient is still wearing braces, the resulting stone model will include portions that represent the teeth as well as portions that represent the braces. However, the portions of the stone model that represent the braces must often be removed in order to provide a stone model suitable for fabrication of a retainer. Removal of the stone braces is usually carried out by a laboratory technician in a tedious manual process using, for example, a hand-held rotary tool with a burr or grinding head. Unfortunately, this manual process tends to increase both the cost and the fabrication time of the resulting retainer. Moreover, this process calls for the technician to estimate the missing surface contour of each tooth while grinding off the stone braces, and this estimation is somewhat subjective.

SUMMARY OF THE INVENTION

The present invention provides methods of using digital data representing the patient's oral structure for dental methods, such as methods of treatment analysis and methods for fabricating a dental retainer. Digital data files representative of both the teeth and the braces are obtained and used to create a revised or new data file representative of the patient's teeth without the braces. This latter digital data file can then be used, for example, to produce a physical model of the patient's dentition without the braces so that subsequent fabrication of the dental retainer is facilitated.

In more detail, the present invention in one aspect relates to a method of preparing a virtual dentition model. The method comprises:

obtaining a digital data file of the patient's oral structure, wherein the digital data file includes first data representing surfaces of the patient's teeth and second data representing a number of orthodontic appliances connected to certain areas of the patient's teeth adjacent the tooth surfaces;

obtaining third data representing at least portions of the patient's tooth surfaces in the certain areas; and combining at least some of the first data with at least some of the third data to provide a virtual dentition model of the patient's teeth with at least a portion of the appliances omitted.

Another aspect of the present invention is directed toward a method of preparing a dental retainer. This method comprises:

obtaining a digital data file of the patient's oral structure, wherein the digital data file includes first data representing surfaces of the patient's teeth and second data representing a number of orthodontic appliances connected to certain areas of the patient's teeth adjacent the tooth surfaces;

obtaining third data representing at least portions of the patient's tooth surfaces in the certain areas;

using at least some of the first data and at least some of the third data to produce a physical model of the patient's dentition with at least a portion of the appliances omitted; and fabricating a retainer using a physical model.

An additional aspect of the invention also relates to a method of fabricating a dental retainer. This method comprises:

obtaining a digital data file representing surfaces within the oral cavity of an orthodontic patient at a time prior to removal of orthodontic brackets that are connected to the patient's teeth;

modifying the digital data file to substantially remove digital data representing the brackets; and fabricating a dental retainer using the modified digital data file.

These and other aspects of the invention are described in more detail below and are illustrated in the accompanying drawings.

DETAILED DESCRIPTION OF THE PREFERRED EMBODIMENTS

Figure 1:
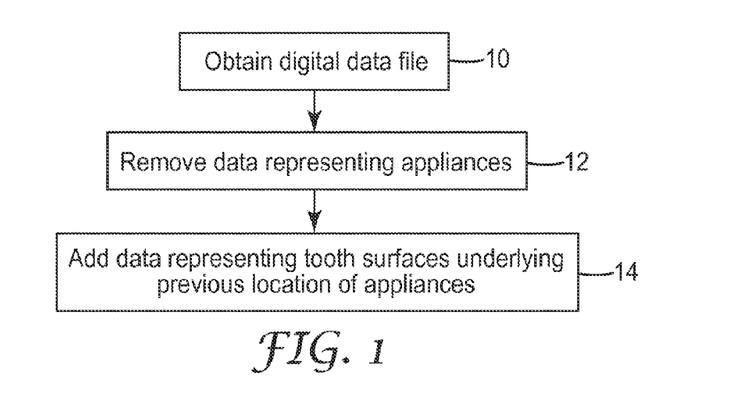
FIG. 1 is a flow diagram illustrating a method for preparing a virtual dentition model according to one embodiment of the present invention.

The flow chart illustrated in FIG. 1 illustrates a method of preparing a virtual dentition model according to one embodiment of the present invention. A first digital data file of the patient's oral structure is obtained, as represented by block 10 in FIG. 1. This first digital data file includes first data that represent surfaces of the patient's teeth and second data that represent a number of orthodontic appliances connected to certain areas of the patient's teeth adjacent the tooth surfaces. As used herein, "data" means digital information that can be used to represent or approximate the configuration of a surface. Examples of data include point clouds or discrete points identified by x, y, and z coordinates in 3D space as well as triangles, polygons or other structures used to form meshes or 3D surfaces connecting the discrete points in 3D space.

Typically, the appliances include orthodontic brackets, orthodontic buccal tubes and other devices that are bonded or otherwise connected to the patient's teeth. The orthodontic appliances may also include archwires that are connected to the brackets and buccal tubes for movement of the teeth to desired positions. Other possible orthodontic appliances include, for example, Class II correctors, bite blocks, arch expanders, and temporary anchorage devices.

The first digital data file obtained in block 10 may be obtained using a hand-held intra-oral scanner such as the intra-oral scanner using active wavefront sampling developed by Brontes Technologies, Inc. (Lexington, Mass.). Other intra-oral scanners may also be used. As another option, the first digital data file described in block 10 may be obtained by using a computed tomography (CT) scanner or an intra-oral contact probe. Although less preferred, as yet another option the first digital data file described in block 10 may be obtained by scanning an impression of the patient's teeth with the appliances, or by scanning a physical model of the patient's teeth with the appliances or by using a contact probe to engage a model of the patient's teeth that includes the appliances. Any suitable scanning technique may be used for scanning the model, such as X-ray radiography, laser scanning, light-based scanning, active wavefront sampling, computed tomography scanning ("CT scanning"), ultrasound imaging and magnetic resonance imaging ("MRI").

Block 12 in FIG. 1 represents the step of removing some or all of the second data representing the orthodontic appliances from the first digital data file obtained in block 10. Optionally, all of the second data representing the orthodontic appliances is removed, leaving only the first data that represent the patient's tooth surfaces. However, since the first digital data file obtained in block 10 does not include data representing the patient's tooth surfaces in areas of the teeth that underlie the orthodontic appliances, the data file obtained in block 12 will not be representative of a complete tooth surface. For example, if an appliance is bonded to a central area located on the facial side of a patient's tooth, the data file obtained in block 12 will have a "hole" or gap, corresponding to a lack of data in that area.

Editing tools in image manipulating software can be used to remove the data representing the orthodontic appliances as described in block 12. An example of image manipulating software is known as "Geomagic Studio" (from Geomagic, Inc. of Research Triangle Park, N.C.), in which portions of an image can be identified and deleted by a technician using a computer mouse or other input device. Optionally, the edited first digital data file is saved in a database as a new digital data file and the original first digital data file is also preserved in the database for future reference if needed.

Next, and as indicated by block 14 in FIG. 1, third data are added to the edited first digital data file obtained in block 12 to fill in the missing gaps that were established once the data relating to the appliances were removed. Optionally, the third data are part of a second digital data file. The third data are then combined with the first data. As one example, a third digital data file may be created by adding the third data to the edited first digital data file as shown in block 14 of FIG. 1. Software known as "ZBrush" (from Pixologic, Inc. of Los Angeles, Calif.) may be used to digitally fine-tune and sculpt the combined data as desired. Preferably, the third data added in block 14 are representative of a surface contour that matches the actual surface contour of the patient's teeth. As a result, the third digital data file obtained after adding the third data from the second digital data file to the remainder of the first digital data file is representative of the patient's tooth surfaces with the orthodontic appliances (including the brackets, buccal tubes and archwires) omitted.

The second digital data file with the third data representing tooth surfaces underlying the appliances as described in block 14 may be provided by various techniques. For example, algorithms can be provided that estimate the configurations of the omitted portions of the tooth surfaces. Software can be used to estimate the curvature of portions of the tooth surface adjacent the omitted surface portions, and fill in missing data using best-fit techniques. An example of suitable software with algorithms for providing data for the omitted portions of the tooth surfaces is the "Geomagic Studio" software mentioned above, using the "fill holes" function and the "curvature-based filling" option. The resultant data file will then include data representing smoothly contoured surfaces provided by the combination of data from the scanned tooth surfaces as well as data provided by the software.

As another option, the third data representing tooth surfaces underlying the appliances as added in block 14 may be carried out by use of a library of model teeth. For example, the library may include data representing the average configuration of each tooth of the oral cavity such as the upper left cuspid tooth. The model tooth data is then scaled as needed by software to match as closely as possible the size of the patient's actual upper left cuspid tooth as obtained in block 10. Next, a portion of the model tooth data that represents an area similar in size and location to the area underlying the appliance on the patient's upper left cuspid tooth is copied from the model tooth data library and combined with the digital data representing the patient's upper left cuspid tooth (with the appliances omitted). This method is repeated for each tooth of interest in the dental arch in order to provide a data file representative of all of the patient's tooth surfaces.

As yet another option, the second digital data file containing data representing the patient's tooth surfaces may be obtained before the onset of orthodontic treatment and before any orthodontic appliances are placed in the oral cavity. This second digital data file, when obtained prior to the beginning of orthodontic treatment, can be advantageously used for other purposes as well. For example, the orthodontic practitioner may desire to obtain a digital data file of the patient's initial malocclusion in order to produce a virtual or physical study model to aid in the diagnosis of the patient and to facilitate treatment planning, and/or to produce a virtual model used in the fabrication of custom orthodontic appliances. Optionally, the digital data file of the patient's teeth before the onset of orthodontic treatment is obtained by a staff member of the patient's general dentist practice before such time as a referral to an orthodontist is made. The digital data file obtained at the general dentist's office is then transmitted to the orthodontist via, e.g., the Internet, optionally accompanied by other data regarding the patient.

The second digital data file of the patient's oral structure before the onset of orthodontic treatment may be obtained using the methods described above, including intra-oral scanning techniques and intra-oral contact probes. Alternatively, the second digital data file may be obtained by scanning an impression of the patient's malocclusion, by scanning a physical model of the patient's malocclusion or by using a contact probe on a physical model of the patient's initial malocclusion. The digital data file of the patient's malocclusion is then divided into data subfiles representing individual teeth. For example, a software program such as the tooth separation software modules of Raindrop Geomagic Dental software from Geomagic, Inc. may be used to separate virtual teeth in the initial malocclusion from each other and from the gingival, so that data representing each tooth can be stored in a separate data subfile.

Next, the third data representing surfaces of the teeth underlying the orthodontic appliances are identified and obtained from the second digital data file, i.e., from the data subfiles representing the individual teeth before the onset of orthodontic treatment. The third data are then combined with the first data (i.e., the data remaining after removal of the appliance data depicted in block 12) in order to provide a third digital data file containing data representing all of the tooth surfaces of interest. This third digital data file is created after undertaking the step described in block 14 in FIG. 1.

As yet another option, the data subfiles of the individual teeth obtained after separation of the teeth from the digital data file of the maloccluded teeth may be registered with, combined with and/or substituted for the subfiles of data representing the individual teeth obtained in block 10. For example, the subfile containing data representing the patient's upper left cuspid tooth in the initial maloccluded state may be copied and used to replace a subfile containing data representing the patient's upper left cuspid tooth near the conclusion of treatment with the appliance as obtained in block 10. The resultant digital data file will thus contain the data that precisely represents the surface of the patient's upper left cuspid tooth, but in an orientation matching the orientation of the patient's upper left cuspid tooth near the conclusion of treatment. Suitable techniques for registering dental tooth surfaces are described in U.S. Provisional Patent Application Ser. No. 61/015,934 entitled "Orthodontic Treatment Monitoring Based on Reduced Images".

The third digital data file obtained in block 14 is advantageous in that it may be used for a variety of purposes. For example, the third digital data file obtained in block 14 may be used to produce a virtual study model or a physical study model of the patient's teeth in final or finished positions, even though the orthodontic appliances may still be connected to the patient's actual teeth at the time such virtual or physical study model is produced. As another option, the third digital data file obtained in block 14 may be used to fabricate orthodontic appliances for subsequent use, such as a series of alignment shells that are used to further move the teeth in incremental steps. The third digital data file may also be used to manufacture a customized orthodontic bracket that is intended to replace another bracket during the course of treatment, or to facilitate the selection of an off-the-shelf bracket that is intended to replace another bracket during the course of treatment. The third digital data file may also be used to produce a physical model that is then used to make a customized bracket, bracket position jig or custom indirect bonding tray. As still another option, the third digital data file obtained in block 14 may be used to fabricate a dental retainer. A variety of retainers are possible, including bonded lingual members (such as polymeric arch bars and solid or braided wire arch members) as well as removable retainers (such as the retainer depicted in FIG. 7).

Figure 2:
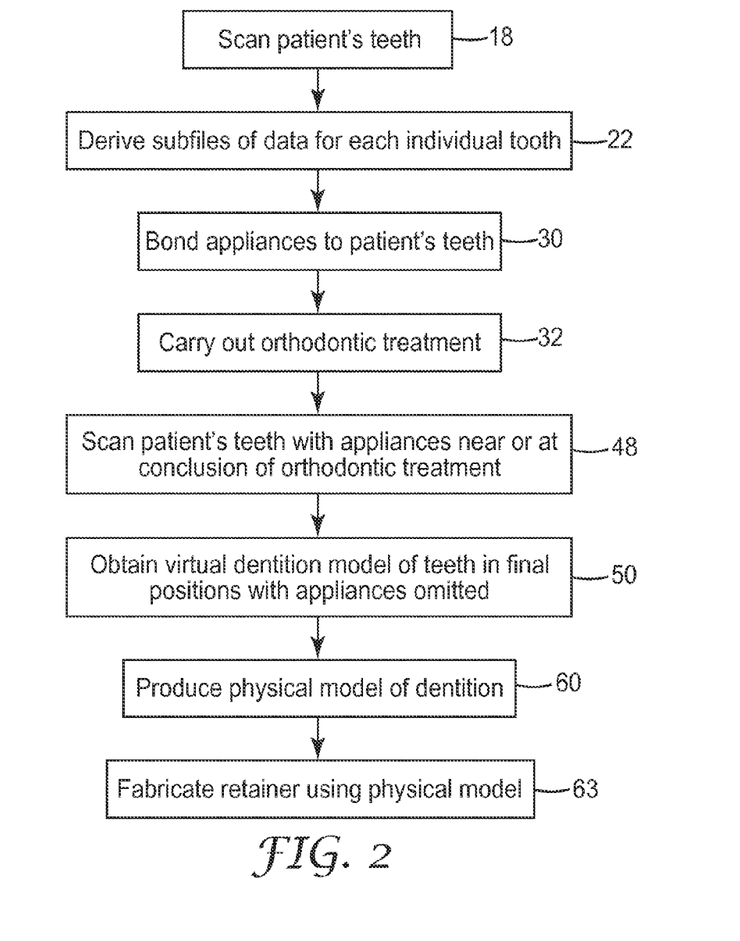
FIG. 2 is a flow chart illustrating one method of preparing a dental retainer according to another aspect of the present invention.
Figure 3:
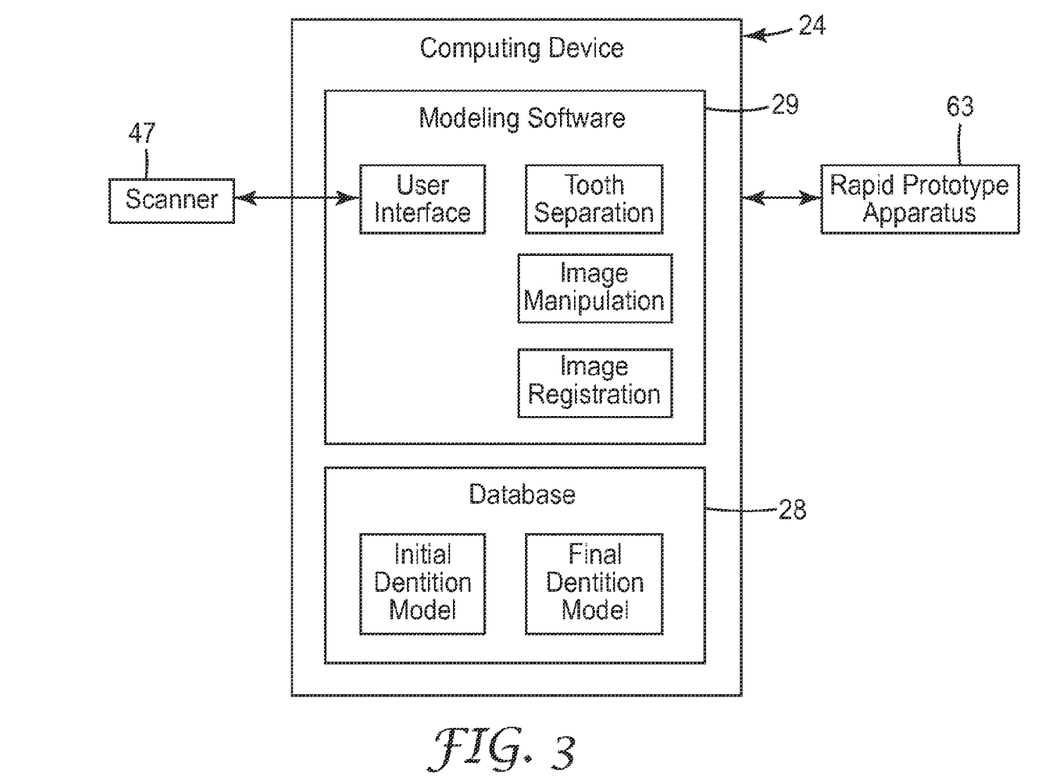
FIG. 3 is a block diagram illustrating an exemplary computer environment in which a computing device receives data representing the patient's teeth and data representing orthodontic appliances for generating a virtual dentition model of the patient's teeth with at least a portion of the appliances omitted.

FIG. 2 is a flow chart illustrating in more detail an exemplary process for fabricating a dental retainer using the third digital data file obtained at the conclusion of block 14 in FIG. 1. FIG. 3 is a block diagram illustrating an exemplary computing device 24 useful for carrying out the process described in FIGS. 1 and 2, and a dental image system of the present invention comprises the computing device 24 along with modeling software 29. In FIG. 2, block 18 describes the step of scanning the patient's teeth prior to the onset of orthodontic treatment to obtain the second digital data file. The second digital data file obtained in block 18 is then processed as described above using tooth separation software module of modeling software 29 (see FIG. 3) to separate the second data file into subfiles representing individual teeth with the gingiva removed, as described in block 22. These subfiles are then stored in a section of the database 28 of the computer device 24 identified as "initial dentition model" in FIG. 3.

Next, and as indicated by block 30 of FIG. 2, a set of orthodontic appliances (such as brackets and buccal tubes) is bonded to the patient's maloccluded teeth. In addition, other orthodontic appliances as may be desired by the practitioner are also put into place in the patient's oral cavity, such as archwires, bite openers, Class II correction devices, arch expanders, temporary anchorage devices and the like. Orthodontic treatment is then carried out as set out in block 32 of FIG. 2 and at least some of the patient's teeth are moved to new positions along the patient's dental arch. A tooth position, as used herein, shall mean either a location of the tooth along the dental arch, an orientation of the tooth at a certain location along the arch, or both.

Figure 4:
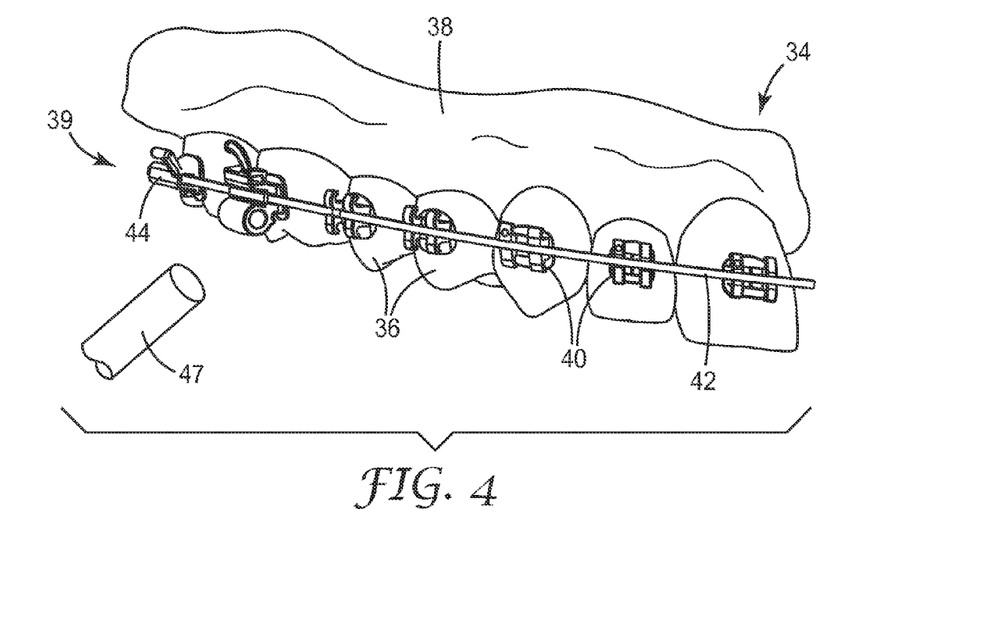
FIG. 4 is an exemplary illustration of a patient's oral structure including teeth and orthodontic appliances along with a scanning device for obtaining digital data representing surfaces of the patient's teeth and the orthodontic appliances.

An exemplary dental arch of an orthodontic patient is illustrated in FIG. 4 as the teeth might appear in desired finished positions or near desired finished positions. In FIG. 4, dental arch 34 includes a number of teeth 36 as well as gum tissue or gingiva 38. A number of orthodontic appliances 39 are connected to the patient's teeth 36, including a set of orthodontic brackets 40 and buccal tube appliances 44. An archwire 42 is placed in slots of the brackets 40. Ends of the archwire 42 are received in the buccal tube appliances 44. Optionally, the buccal tube appliances 44 may be connected to bands (not shown) that encircle the patient's molar teeth.

In FIG. 4, the intra-oral scanner 47 is schematically depicted and optionally is the same scanner used to scan the patient's teeth prior to the onset of orthodontic treatment as described in block 18. Scanner 47 is used to scan the patient's teeth 36 as indicated by block 48 of FIG. 2 at a point in time that is at the conclusion or near the conclusion of the orthodontic treatment program, such that the teeth 36 are in their desired final positions or are near their desired final positions. Although the scanner 47 at this time obtains data (i.e., first data) representing the configuration of a portion of the surfaces of the patient's teeth 36 as well as data (i.e., second data) representing the configuration of appliances 39 connected to the patient's teeth 36, the scanner 47 does not obtain data representing the configuration of areas of the tooth surfaces that underlie the appliances 39, since the appliances 39 block the scanner 47 from receiving such data.

As one example, if the estimated time for fabrication of a dental retainer and shipment of the retainer to the practitioner's office is three weeks, the scan of the patient's teeth 36 as indicated by block 48 may be carried out three weeks ahead of the estimated time for completion of orthodontic treatment. In this manner, there is sufficient time to make the retainer and transport the retainer to the practitioner's office for arrival by the estimated time that the treatment program with appliances 39 will finish. Consequently, the dental retainer may be put in place in the patient's oral cavity within minutes of the time that the orthodontic appliances 39 such as the brackets 40, archwire 42 and buccal tubes 44 have been removed.

Figure 5:
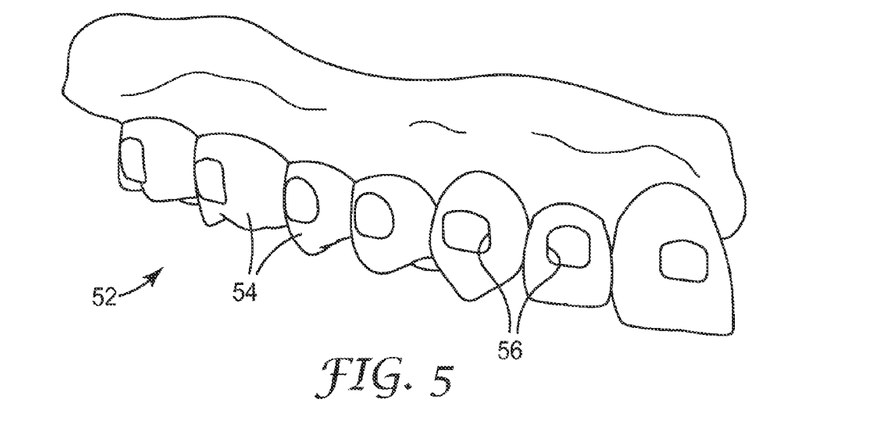
FIG. 5 is an exemplary illustration of a virtual model of the patient's teeth shown in FIG. 4 with the appliances omitted.

Next, a virtual dentition model 52 of the teeth 36 in finished or post-treatment positions is obtained with the brackets 40, the archwire 42 and the buccal tube appliances 44 omitted as described in block 50. As shown in FIG. 5, this virtual dentition model 52 preferably lacks all data representing each of the orthodontic appliances 39. Preferably, the dentition model 52 is also provided with data representing smoothly curved surfaces that have the same or substantially the same configuration as the patient's tooth surfaces that lie under the appliances 39. The virtual dentition model 52 described in block 50 may be obtained through the methods described above, including the methods described in blocks 10-14 of FIG. 1.

The exemplary virtual dentition model 52 shown in FIG. 5 is obtained after the scanner 22 has scanned the patient's teeth 36 as shown in FIG. 4, and after the image manipulation software shown in FIG. 3 has redacted data representing the appliances 39. As shown in FIG. 5, each of the virtual teeth 54 of the dentition model 52 is consequently left with a "hole" or gap 56 of data representing the surface of the teeth 36 in areas previously covered by the appliances 39.

Figure 6:
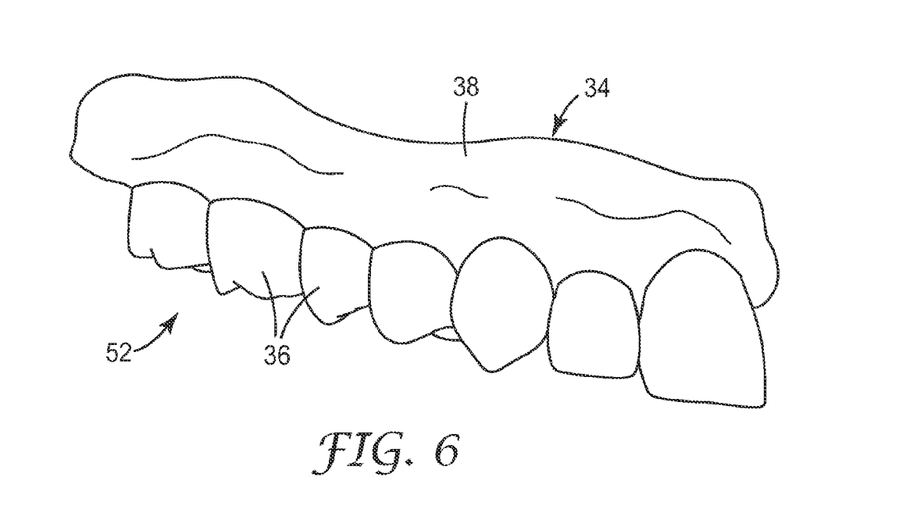
FIG. 6 is a view somewhat similar to FIG. 5 except that the computing device has provided data representing surfaces of the teeth in areas where the appliances were previously located.

FIG. 6 illustrates the virtual dentition model 52 shown in FIG. 5, except that the modeling software of computing device 24 has provided data representing surfaces of the teeth 36 in areas previously corresponding to gaps 56. Preferably, and as shown, the resulting virtual tooth surface is smoothly curved and continuous, matching the shape of the patient's actual tooth surface. The modeling software 29 includes a rendering module that preferably is capable of rendering a digital representation of any useful views of the data representations mentioned above for a technician or orthodontic practitioner, including the views shown in FIGS. 4-6.

Figure 7:
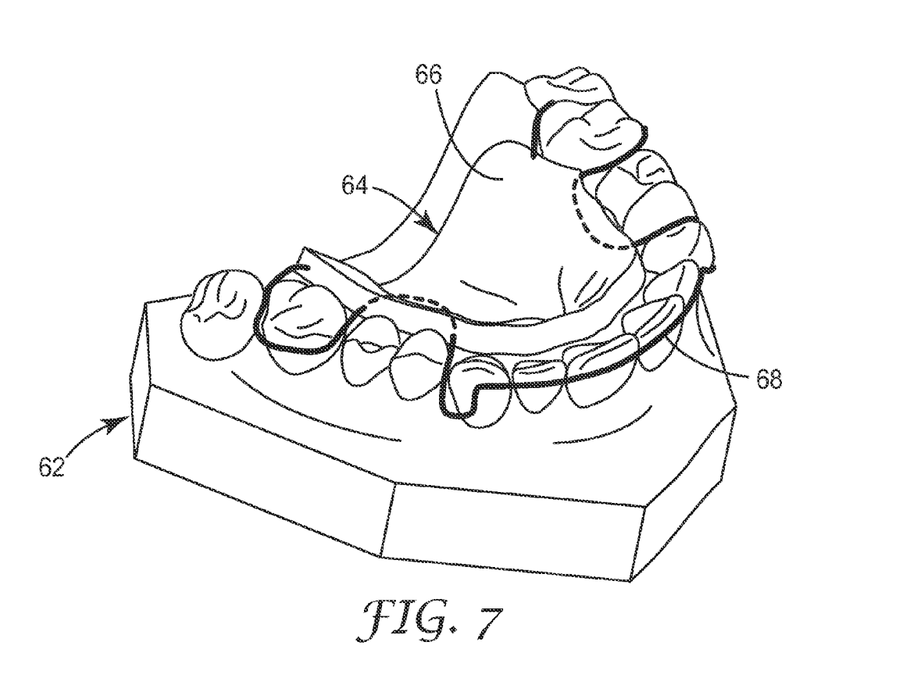
FIG. 7 is an exemplary illustration of a physical model that has been produced using the virtual dentition model shown in FIG. 6, along with components used in the fabrication of a custom retainer for the patient.

Next, a physical model of the virtual dentition model 52 is produced as described in block 60 of FIG. 2. An exemplary physical model 62 is shown in FIG. 7. One method of producing the physical model 62 as described in block 60 is carried out using data representing the virtual dentition model 52 in conjunction with a rapid prototyping process to make a replica. In FIG. 3, the modeling software 29 interacts with rapid prototyping apparatus 63 to make the physical replica of dentition model 52. As used herein, rapid prototyping is the process of generating an object directly from digital data, such as digital data representing the shape of the object. Examples of suitable rapid prototyping processes include solid freeform fabrication such as 3D printing processes, stereolithography methods, fused deposition modeling, laminated object manufacturing, laser engineered net shaping, selective laser sintering, shape deposition manufacturing and solid ground curing. Issued U.S. Pat. Nos. 5,340,656, 5,490,882, 5,204,055, 5,518,680, 5,490,962, 5,387,380, 5,700,289, 5,518,680 and 4,672,032 describe examples of rapid prototyping processes. An example of a suitable rapid prototyping apparatus 63 is a 3D printing machine, such as the Eden brand 500V printer from Objet Geometries Ltd., using FullCure 720 acrylic-based photopolymer printing material (also from Objet Geometries Ltd.). Another example of a rapid prototyping process is the use of CAD-CAM software to direct a milling machine to mill the dental arch replica.

Next, an impression of the rapid prototype replica is made using an impression material. Suitable impression materials include dental impression materials such as alginate or polyvinylsiloxane. Examples of commercially available dental impression materials include Position Penta Quick brand, Dimension brand, Express brand and Imprint II brand impression materials from 3M ESPE (St. Paul, Minn.). Duplicating materials may also be used, such as Z-Dupe brand duplication silicone from Henry Schein Inc. (Melville, N.Y.).

In this example, the physical model 62 is produced using the impression of the rapid prototype replica. Preferably, the material used to make the physical model 62 does not shrink or expand significantly upon hardening and, once hardened, is heat resistant to allow fabrication of dental appliances such as retainers that are constructed using heat. Optionally, the physical model 62 can resist distortion by localized temperatures exceeding 1970° C. that may be encountered during soldering, brazing and welding operations. An example of a suitable material for the physical model 62 is dental stone, such as plaster of Paris.

However, other model matrix materials may be also be used, such as investment materials. Typical investment materials include gypsum or a refractory filler, such as silica in the form of cristobalite, quartz, leucite, zirconia, hafnia, zircon, alumina, magnesia, aluminosilicate, cordierite, mica, silicon nitride, silicon carbide, silica-alumina-nitrides, mullite, garnet, or mixtures thereof, in combination with a binder. Binders may include but are not limited to inorganic and organic binders, or mixtures thereof. Organic binders include, but are not limited to, polyvinyl pyrrolidine, polyvinyl alcohol, polyvinyl acetate, polyvinyl chloride, polyvinyl butryal and polystyrene, or mixtures thereof. Inorganic binders include, but are not limited to, magnesium oxide, ammonium phosphate, colloidal silica, calcium sulfate, magnesium phosphate, alkaline silicates, silica hydrosol, colloidal clays, or mixtures thereof.

As another option, the digital data representing the virtual dentition model 52 may be used in conjunction with rapid prototyping processes to directly form a negative mold for the physical model 62. Examples of suitable rapid prototyping processes for making a negative mold include the rapid prototyping processes for making a dental replica as described above. Preferably, the negative mold for making the physical model 62 is configured such that it can be flexed, stretched, fractured, or disassembled to facilitate release of the physical model 62. Examples of suitable negative molds for making physical dentition models such as physical models 62 are described in pending Provisional U.S. Patent Application 60/975,687 entitled "DIGITALLY FORMING A DENTAL MODEL FOR FABRICATING ORTHODONTIC LABORATORY APPLIANCES".

Next, retainer 64 is fabricated using the physical model 62 as shown in FIG. 7 and as indicated by box 63 of FIG. 2. The exemplary retainer 64 depicted in FIG. 7 includes a shaped polymeric body 66 as well as a custom-bent wire 68 that is partially embedded in the body 66. The body 66 has a configuration matching a palatal region of the patient's oral cavity. The wire 68 in this example is shaped to engage the facial surfaces of the patient's anterior teeth and extend around the patient's upper first molar teeth, although other constructions are also possible.

Other types of retainers are also possible. For example, the methods described above can be used to manufacture custom-formed bonded retainers, such as bars made of polymeric or metallic material that are bonded to the lingual surfaces of the patient's teeth. Preferably the retainers are fabricated while the orthodontic appliances are still in place. Other types of bonded retainers are also possible, such as an assembly of braided wires that is custom-shaped and then bonded in place on the lingual surfaces of the patient's teeth. Advantageously, using the methods described herein, the bonded retainers can be fixed to the patient's teeth immediately before removing the brackets 40, the buccal tube appliances 44 and the archwires 42 from the patient's teeth, such that the teeth cannot drift from their intended final positions. As another example, lingual retainers may be fabricated and shipped to the orthodontist during the time that lingual orthodontic appliances remain bonded to the patient's teeth.

All patents and patent applications mentioned above are incorporated by reference herein. Additionally, a number of other variations to the invention described above are also possible. Consequently, the invention should not be deemed limited to the presently preferred embodiments as set out in detail above, but instead only by a fair scope of the claims that follow along with their equivalents.

The invention claimed is:

1. A method of preparing a virtual dentition model comprising:
    obtaining a digital data file of the patient's oral structure, wherein the digital data file includes first data representing surfaces of the patient's teeth and second data representing a number of orthodontic appliances connected to certain areas of the patient's teeth adjacent the tooth surfaces;
    obtaining third data representing at least portions of the patient's tooth surfaces in the certain areas, wherein the third data represents the patient's oral structure at a time that is prior to the time of connecting the orthodontic appliances to the teeth, and wherein the first data represents the teeth in certain positions, and wherein the third data represents the patient's teeth in positions, at least some of which are different than the positions of the patient's teeth represented by the first data; and
    combining at least some of the first data with at least some of the third data to provide a virtual dentition model of the patient's teeth with at least a portion of the appliances omitted, wherein the virtual dentition model includes one or more surfaces that have the same or substantially the same configuration as the patient's tooth surfaces in the certain areas; and
    fabricating a dental retainer based at least in part on the virtual dentition model, wherein the act of fabricating the dental retainer is carried out before the time that the orthodontic appliances are removed from the patient's teeth.

2. A method of preparing a virtual dentition model according to claim 1 wherein the third data is obtained by use of best-fit algorithms.

3. A method of preparing a virtual dentition model according to claim 1 wherein the third data is provided from a library containing data of model tooth structure.

4. A method of preparing a virtual dentition model according to claim 1 and including the act of producing a physical model of the patient's dentition using the virtual dentition model.

5. A method of preparing a virtual dentition model according to claim 4 wherein the act of producing a physical model of the patient's dentition is carried out by using the virtual dentition model to make a negative mold for the physical model.

6. A method of preparing a virtual dentition model according to claim 1 wherein the act of combining at least some of the first data with at least some of the third data includes the act of removing at least some of the second data from the digital data file.

7. A method of fabricating a dental retainer comprising:
    obtaining a digital data file of the patient's oral structure, wherein the digital data file includes first data representing surfaces of the patient's teeth and second data representing a number of orthodontic appliances connected to certain areas of the patient's teeth adjacent the tooth surfaces;

obtaining third data representing at least portions of the patient's tooth surfaces in the certain areas, wherein the third data represents the patient's oral structure at a time that is prior to the time of connecting the orthodontic appliances to the teeth, and wherein the first data represents the teeth in certain positions, and wherein the third data represents the patient's teeth in positions, at least some of which are different than the positions of the patient's teeth represented by the first data; and using at least some of the first data and at least some of the third data to produce a physical model of the patient's dentition with at least a portion of the appliances omitted, wherein the physical model includes one or more surfaces that have the same or substantially the same configuration as the patient's tooth surfaces in the certain areas; and fabricating a retainer using the physical model, wherein the act of fabricating the dental retainer is carried out before the time that the orthodontic appliances are removed from the patient's teeth.

8. A method of fabricating a dental retainer according to claim 7 wherein the act of using at least some of the first data and at least some of the third data to produce a physical model is carried out by a method comprising the acts of (1) using a rapid prototyping process to make a dental replica, (2) taking an impression of the dental replica, and (3) using the impression to make the physical model.

9. A method of fabricating a dental retainer according to claim 8 wherein the act of using at least some of the first data and at least some of the third data to produce a physical model is carried out by using the rapid prototyping process to make a negative mold for the physical model.

10. A method of fabricating a dental retainer according to claim 7 wherein the first data represents the teeth in certain positions, and wherein the third data represents the patient's teeth in positions, at least some of which are different than the certain positions.

11. A method of fabricating a dental retainer according to claim 7 wherein the third data is obtained by use of best-fit algorithms.

12. A method of fabricating a dental retainer according to claim 7 wherein the third data is provided from a library containing data of model tooth structure.

13. A method of fabricating a dental retainer according to claim 7 wherein the act of fabricating the retainer is carried out before such time as the appliances are disconnected from the patient's teeth.

14. A method of fabricating a dental retainer comprising:
obtaining a digital data file representing surfaces within the oral cavity of an orthodontic patient at a time prior to removal of orthodontic brackets that are connected to the patient's teeth, wherein the act of obtaining the digital data file occurs at a time when the patient's teeth are in positions, at least some of which are different than the positions of the patient's teeth before the orthodontic brackets were connected;

modifying the digital data file to substantially remove digital data representing the brackets, wherein the modifications include providing one or more surfaces that have the same or substantially the same configuration as the patient's tooth surfaces covered by the brackets, the surfaces representing the patient's oral structure at a time that is prior to the time of connecting the orthodontic brackets to the teeth; and fabricating a dental retainer using the modified digital data file, wherein the act of fabricating the dental retainer is carried out before the time that the orthodontic appliances are removed from the patient's teeth.

15. A method of fabricating a dental retainer according to claim 14 and including the act of producing a physical model of the patient's dentition with the brackets omitted.

16. A method of fabricating a dental retainer according to claim 15 wherein the act of producing a physical model is carried out at least in part by using a rapid prototyping process.

17. A method of fabricating a dental retainer according to claim 16 wherein the act of producing a physical model is carried out by a method comprising the acts of (1) using the rapid prototyping process to make a dental replica, (2) taking an impression of the dental replica, and (3) using the impression to make the physical model.

18. A method of fabricating a dental retainer according to claim 16 wherein the act of producing a physical model is carried out by using the rapid prototyping process to make a negative mold for the physical model.

19. A method of fabricating a dental retainer according to claim 14 and including the act of providing the dental retainer to the patient during the same day that the orthodontic brackets are removed from the patient's teeth.

20. A method of fabricating a dental retainer according to claim 14 wherein the act of fabricating the dental retainer is carried out before the time that the orthodontic brackets are removed from the patient's teeth.

21. A system comprising:
a computing device; and
software executing on the computing device, wherein the software carries out the steps of:
obtaining a digital data file of the patient's oral structure, wherein the digital data file includes first data representing surfaces of the patient's teeth and second data representing a number of orthodontic appliances connected to certain areas of the patient's teeth adjacent the tooth surfaces;

obtaining third data representing at least portions of the patient's tooth surfaces in the certain areas the third data represents the patient's oral structure at a time that is prior to the time of connecting the orthodontic appliances to the teeth, and wherein the first data represents the teeth in certain positions, and wherein the third data represents the patient's teeth in positions, at least some of which are different than the positions of the patient's teeth represented by the first data; and combining at least some of the first data with at least some of the third data to provide a virtual dentition model of the patient's teeth with at least a portion of the appliances omitted, wherein the virtual dentition model includes one or more surfaces that have the same or substantially the same configuration as the patient's tooth surfaces in the certain areas; and creating a virtual dental retainer based at least in part on the virtual dentition model, wherein the act of creating the virtual dental retainer is carried out before the time that the orthodontic appliances are removed from the patient's teeth.

* * * * *

UNITED STATES PATENT AND TRADEMARK OFFICE
CERTIFICATE OF CORRECTION

| | | |
|---|---|---|
| PATENT NO. | : 8,738,165 B2 | Page 1 of 1 |
| APPLICATION NO. | : 12/808214 | |
| DATED | : May 27, 2014 | |
| INVENTOR(S) | : David Cinader | |

It is certified that error appears in the above-identified patent and that said Letters Patent is hereby corrected as shown below:

In the Specification

Column 1
Line 64, delete "terepthalate" and insert -- terephthalate --, therefor.

Column 9
Line 27, delete "butryal" and insert -- butyral --, therefor.

In the Claims

Column 11
Line 13, in Claim 7, after "data;" delete "and".

Signed and Sealed this
Twenty-third Day of June, 2015

Michelle K. Lee
*Director of the United States Patent and Trademark Office*